(12) United States Patent
Zilberman et al.

(10) Patent No.: US 8,889,773 B2
(45) Date of Patent: Nov. 18, 2014

(54) METAL PHOSPHONATE FLAME RETARDANT AND METHOD PRODUCING THEREOF

(75) Inventors: Joseph Zilberman, Haifa (IL); Sergei V. Levchik, Croton-on-Hudson, NY (US); Andrew Gregor, Wingdale, NY (US); Pierre Georlette, Omer (IL); Yoav Bar Yaakov, Tel Aviv (IL); Gideon Shikolski, Kiryat Motzkin (IL)

(73) Assignee: ICL-IP America Inc., Ardsley, NY (US)

( * ) Notice: Subject to any disclaimer, the term of this patent is extended or adjusted under 35 U.S.C. 154(b) by 0 days.

(21) Appl. No.: 13/806,199

(22) PCT Filed: Jun. 21, 2011

(86) PCT No.: PCT/US2011/041220
§ 371 (c)(1),
(2), (4) Date: Feb. 27, 2013

(87) PCT Pub. No.: WO2011/163207
PCT Pub. Date: Dec. 29, 2011

(65) Prior Publication Data
US 2013/0165564 A1    Jun. 27, 2013

Related U.S. Application Data

(60) Provisional application No. 61/358,240, filed on Jun. 24, 2010.

(51) Int. Cl.
| | |
|---|---|
| *C08K 3/32* | (2006.01) |
| *G07F 19/00* | (2006.01) |
| *C07F 9/40* | (2006.01) |
| *C07F 9/48* | (2006.01) |
| *C07F 9/08* | (2006.01) |
| *C09K 21/12* | (2006.01) |
| *C08K 5/5317* | (2006.01) |
| *C07F 19/00* | (2006.01) |

(52) U.S. Cl.
CPC ............... *G08K 3/32* (2013.01); *G07F 9/4006* (2013.01); *C09K 21/12* (2013.01); *C08K 5/5317* (2013.01); *C07F 19/00* (2013.01)
USPC ............ 524/130; 524/123; 556/174; 558/133

(58) Field of Classification Search
CPC ............. C08K 3/32; C07F 19/00; C07F 9/40; C07F 9/48; C07F 9/08
USPC ..................... 524/123, 130; 556/174; 558/133
See application file for complete search history.

(56) References Cited

U.S. PATENT DOCUMENTS

| | | | |
|---|---|---|---|
| 4,939,285 A | 7/1990 | Wies et al. | |
| 4,972,011 A | 11/1990 | Richardson et al. | |
| 4,973,727 A | 11/1990 | Gainer et al. | |
| 4,981,926 A | 1/1991 | Pham et al. | |
| 5,102,932 A | 4/1992 | Gainer et al. | |
| 5,109,099 A | 4/1992 | Pham et al. | |
| 5,208,317 A | 5/1993 | Pham et al. | |
| 5,376,714 A | 12/1994 | Yates | |
| 6,184,405 B1 * | 2/2001 | Kleiner et al. | ................ 556/174 |

FOREIGN PATENT DOCUMENTS

| | | |
|---|---|---|
| DE | 19645125 A1 | 5/1998 |
| EP | 0327496 A2 | 8/1989 |
| EP | 0343109 B1 | 11/1989 |
| EP | 0356633 A1 | 3/1990 |
| EP | 0356634 A1 | 3/1990 |
| EP | 0430876 A1 | 6/1991 |
| EP | 0446169 A1 | 9/1991 |
| EP | 0522653 A1 | 1/1993 |
| GB | 2211850 A | 7/1989 |
| WO | WO 00/12608 | 3/2000 |
| WO | WO 2007/081904 A1 | 7/2007 |

OTHER PUBLICATIONS

Maeda et al.—"Characterization and Gas Adsorption Properties of Aluminum Methylphosphonates with Organically Lined Unidimensional Channels", (J. Phys. Chem. B 1997, 101, 4402-4412).*

* cited by examiner

*Primary Examiner* — Ling Choi
*Assistant Examiner* — Ronald Grinsted
(74) *Attorney, Agent, or Firm* — Dilworth & Barrese, LLP (57) ABSTRACT

There is provided herein an aluminum methyl methylphosphonate in crystalline form wherein 90% of the aluminum methyl methylphoshponate has a particle size of less than 10 microns, and wherein the aluminum methyl methylphosphonate is obtained by the process of reacting aluminum hydroxide with dimethyl methylphosphonate in the presence of a catalyst.

35 Claims, 10 Drawing Sheets

Figure 1  XRD of ATH

Figure 2  TGA of ATH

Figure 3  TGA of final product of Comparative Example 1

Figure 4  XRD of final product of Comparative Example 1

Figure 5   TGA of final product of Example 2

Figure 6  XRD spectra of AMMP products of Examples 2 (upper) and 3 (lower) (washed AMMP)

Figure 7  SEM image of AMMP obtained in Example 2

Figure 8  TGA of final product of Example 3

Figure 9 TGA of final product of Example 4

Figure 10 SEM image of AMMP obtained in Comparative Example 5

METAL PHOSPHONATE FLAME RETARDANT AND METHOD PRODUCING THEREOF

This application claims priority to U.S. provisional application No. 61/358,240 filed on Jun. 24, 2010.

FIELD OF THE INVENTION

This patent relates to fine crystalline aluminum methyl methylphosphonate obtained by reacting dimethyl methylphosphonate with aluminum hydroxide in the presence of a catalyst.

BACKGROUND OF THE INVENTION

Aluminum methyl methylphosphonate (AMMP) is a flame retardant additive that has been used for various polymers.

Since AMMP does not melt during processing it is very important to achieve good dispersion of the AMMP in the polymer. It is well known in the art that good dispersion is achieved with fine powders with a narrow particle size distribution. Polymer composites with evenly distributed flame retardant particles have better flame retardant properties and better physical properties. If the particles are small (i.e., an average particle size of less than 5 microns) translucent or transparent polymer composites can be obtained.

Among the few known methods for preparing AMMP, the most frequently encountered ones are those based on the use of dimethyl methylphosphonate (DMMP) as a starting material. In one known method, DMMP reacts with an aqueous solution of a strong base, for example KOH or NaOH to form the water soluble alkali salt of methyl methylphosphonic acid. The same salts can also be prepared by reacting anhydrous DMMP with an alkali metal. The alkali salt of methyl methylphosphonic acid so obtained reacts further with a water soluble aluminum salt (e.g $AlCl_3$ or $Al_2(SO_4)_3$) to precipitate the water insoluble AMMP. This process requires water washing of the AMMP in order to remove sodium chloride or sulfate. The washing and filtering has to be repeated 4-5 times in order to achieve a high purity. This results in about 15 to 20% loss in the yield. Furthermore, dry AMMP forms a dense cake which must be milled in order to be useful as a flame retardant.

AMMP is also prepared by the reaction of DMMP with anhydrous aluminum chloride or an aluminum alkoxide, e.g. aluminum iso-propoxide. However, these preparations result in undesired and hazardous by-products such as methyl chloride, methylalkyl ethers, carbon monoxide, methane, and others. Furthermore, aluminum alkoxides are relatively expensive and difficult to handle.

Another approach for making AMMP involves the direct reaction of aluminum metal, in the form of aluminum foil with DMMP. This reaction requires prolonged heating (48 hours) at reflux, and the continuous addition of magnesium as a co-reactant. The resultant AMMP is contaminated with magnesium methyl methyl phosphonate.

Other processes can produce AMMP in a good yield by the reaction of DMMP with a finely divided form of aluminum hydroxide (ATH). According to these processes, the average particle size of the ATH has to be below 2 microns to make its reaction with DMMP more efficient, even though the reaction time is still undesirably long. Furthermore, such a reaction does not go to completion within a reasonable time even with ATH of such a small particle size. Unreacted ATH remains in the AMMP and therefore limits the application of the AMMP, because of the lower thermal stability of ATH. Such ATH consisting of such fine particles, is much more expensive compared to a variety of other coarser, but much cheaper grades of this product.

Another process comprises the reaction of DMMP with aluminum hydroxide having an average particle size of less than 2 microns, in the presence of large quantities of commercially unavailable methylphosphonic acid or methyl methylphosphonic acid. The latter is also used as a sole starting material for making AMMP by reaction with ATH in a polar organic solvent.

SUMMARY OF THE INVENTION

In view of the above, it can be seen that a need exists for very fine uniform crystalline AMMP.

It is also seen that a new route is required for the preparation of fine, uniform, crystalline AMMP, which avoids the aforementioned disadvantages, proceeds within a relatively short reaction time, is based on cheap and available commercial raw materials, and provides the final AMMP in high yield and purity. In addition, it would be advantageous to have a process for making AMMP which results in AMMP that does not melt below 400° C.

The inventors herein have unexpectedly found that the time of the reaction between DMMP and chemically non-active aluminum hydroxide, can be shortened significantly by using an efficient catalyst to provide fine uniform crystalline AMMP in a quantitative yield and with excellent purity.

There is provided herein in one embodiment aluminum methyl methylphosphonate in crystalline form, wherein 90% of the aluminum methyl methylphosphonate particles have a particle size of less than 10 microns and wherein the aluminum methyl methylphosphonate is obtained by the process of reacting aluminum hydroxide with dimethyl methylphosphonate in the presence of a catalyst.

There is provided herein, in another embodiment, a process comprising reacting aluminum hydroxide with dimethyl methylphosphonate in the presence of a catalyst.

DETAILED DESCRIPTION OF PREFERRED EMBODIMENTS

There is provided herein fine, uniform, crystalline AMMP, which is prepared by a new process comprising reacting DMMP with ATH in the presence of an effective amount of a catalyst. The AMMP produced by the process herein has a desirably fine particle size, e.g., wherein 90% by weight of the AMMP particles have a particle size of less than 10 microns, and/or, wherein the AMMP is produced in a time period that is shorter than an equivalent process that is conducted in the absence of a catalyst.

Typical reaction temperatures for the reaction between ATH and DMMP are between about 150 to about 181° C., preferably from about 170 to about 181° C. If higher temperatures are desired, the reaction can be performed under pressure. According to a preferred embodiment of the invention, the reaction can be carried out under reflux using an excess of DMMP (boiling point 181° C.) as the reaction solvent and dispersing medium for the ATH and AMMP. Alternatively, a suitable high boiling solvent inert under the process conditions can be employed, such as the non-limiting examples of dichlorobenzenes, mesitylene and high boiling petroleum ether. The DMMP/ATH molar ratio for the reaction is in the range of 3 to 15, more preferably in the range of 5 to 10. Using a molar ratio greater than 15 is inexpedient due to the need to distill and recycle the larger quantities of DMMP. When the DMMP/aluminum hydroxide molar ratio is below 5 it becomes difficult to achieve complete conversion of the aluminum hydroxide due to the fact that the AMMP forms a coat on the surface of the unreacted aluminum hydroxide and stops the reaction well before completion thereby producing an unsatisfactory yield. Furthermore, stirring of reaction media containing a less than 5 times molar excess of DMMP becomes problematic towards the end of the reaction because a thick dispersion of AMMP is formed.

Surprisingly, the process of the invention does not produce any hazardous by-products. Unreacted DMMP may be recycled to the process and the methanol formed may be easily removed.

In one non-limiting embodiment the catalyst is selected from the group consisting of phase transfer catalysts (PTC), thermally stable tertiary amines having a boiling point higher than about 140° C. and thermally stable phosphines having a boiling point higher than about 140° C. and combinations thereof.

In one another embodiment of the invention the PTC is a quarternary phosphonium salt described by the formula:

wherein each $R_1$, $R_2$, $R_3$ and $R_4$ independently is a hydrocarbyl or inertly substituted hydrocarbyl radical containing from 1 to about 16 carbon atoms, preferably from 1 to about 6 carbon atoms, Y is an anion and m is the valence of the anion. In one embodiment, Y is an anion selected from the group consisting of bromide, fluoride, chloride, iodide, acetate, acetate complex, acetate/acetic acid complex, phosphate, phosphate complex, hydrogen sulfate and hydroxide. In one embodiment, m can be 1, 2 or 3.

Preferred quaternary phosphonium salts are selected from the group consisting of, but not limited to, for example, tetrabutylphosphonium chloride, tetrabutylphosphonium bromide, tetrabutylphosphonium iodide, tetrabutylphosphonium acetate complex, tetraphenylphosphonium chloride, tetraphenylphosphonium bromide, tetraphenylphosphonium iodide, ethyltriphenylphosphonium chloride, ethyltriphenylphosphonium bromide, ethyltriphenylphosphonium iodide, ethyltriphenylphosphonium acetate complex, ethyltriphenylphosphonium phosphate complex, n-propyltriphenylphosphonium chloride, n-propyltriphenylphosphonium bromide, propyltriphenylphosphonium iodide, butyltriphenylphosphonium chloride, butyltriphenylphosphonium bromide, butyltriphenylphosphonium iodide, ethyltri-p-tolylphosphonium acetate/acetic acid complex, ethyltriphenylphosphonium acetate/acetic acid complex, hexadecyltributylphosphonium bromide, or combinations thereof, and the like, as are described in U.S. Pat. Nos. 5,208,317, 5,109,099 and 4,981,926, the contents of each of which are attached hereto as part of the subject disclosure and are incorporated herein by reference in their entirety.

In yet another embodiment of the invention, the PTC is a quaternary ammonium salt. Preferred catalysts among quaternary ammonium salts are selected from the group consisting of, but not limited to, for example, tetraethylammonium bromide, tetrabutylammonium chloride, tetrabutylammonium bromide, tetrabutylammonium hydrogen sulfate, methyltrioctylammonium chloride, benzyl triethylammonium chloride and combinations thereof.

Tertiary amine catalysts, which are thermally stable under the conditions of the present process and which have a boiling point higher than about 140° C. are those such as, for example, 2- or 4-(dimethylamino)pyridine and combinations thereof.

In another embodiment of this invention the tertiary amine catalysts are imidazole type compounds represented by the following general formula:

wherein each $R_1$, $R_2$, $R_3$ and $R_4$ independently is a hydrogen, or hydrocarbyl or inertly substituted hydrocarbyl radical, containing from 1 to about 16 carbon atoms, preferably from 1 to about 6 carbon atoms.

Preferred imidazole type catalysts are selected from but not limited to the group 1-methylimidazole; 2-methyl imidazole; 2-ethylimidazole, 2-propylimidazole, 2-butylimidazole, 2-pentylimidazole, 2-hexylimidazole, 2-cyclohexylimidazole, 2-phenylimidazole, 2-nonyl-imidazole, 2-undecylimidazole, 2-heptadecylimidazole, 2-phenyl-4-methylimidazole, 1-benzylimldazole, 1-ethyl-2-methylbenzimidazole, 2-methyl-5,6-benzimidazole, 1-vinylimidazole, 1-allyl-2-methylimidazole, 2-cyanoimidazole, 2-chloroimidazole, 2-bromoimidazole, 1-(2-hydroxypropyl)-2-methylimidazole, 2-phenyl-4,5-dimethylolimidazole, 2-phenyl-4-methyl-5-hydroxymethylimidazole, 2-chloromethylbenzimidazole, 2-hydroxybenzimidazole, 2-ethyl-4-methylimidazole; 2-cyclohexyl-4-methylimidazoles; 4-butyl-5-ethylimidazole; 2-butoxy-4-allylimidazole; 2-carboethyoxy-butylimidazole, 4-methytimidazole; 2-octyl-4-hexylimidazole; 2-methyl-5-ethylimidazole; 2-ethyl-4-(2-ethylamino)imidazole; 2-methyl-4-mercaptoethylimidazole; 2,5-chloro-4-ethylimidazole; and mixtures thereof. Preferred are the alkyl-substituted imidazoles; 2,5-chloro-4-ethylimidazole and mixtures thereof.

Phosphine catalysts, which are thermally stable under the conditions of the present process and which have a boiling point higher than about 140° C., can be those selected from the group consisting of triaryl phosphines, alkyl diaryl phosphines, dialkyl aryl phosphines, trialkyl phosphines, where the aryl is a substituted or unsubstituted phenyl and the alkyl is a linear, branched or cyclic $C_4$-$C_{16}$ hydrocarbyl radical, and combinations thereof. One specific embodiment of a phosphine catalyst is triphenyl phosphine.

Other suitable catalysts will be easily recognized by the skilled person. Especially suitable catalysts are phase transfer catalysts such as ethyltriphenylphosphonium acetate, tetrabutylphosphonium bromide, tetrabutylammonium bromide, and catalysts such as 4-(dimethylamino)pyridine, triphenyl phosphine and 2-methylimidazole.

The concentration of the catalyst can be selected by those skilled in the art for specific reaction conditions. Illustrative—but non-limiting concentrations of the catalyst are in the range of about 0.1 to about 5 wt. % (weight percent) relative to the initial amount of aluminum hydroxide. The preferred concentrations of the catalyst are in the range of 0.4 to 2 wt. % relative to the initial amount of aluminum hydroxide.

The typical reaction time of the reaction described herein between ATH and DMMP is between about 3 to about 20 hours, preferably between about 5 to about 15 hours.

The aluminum hydroxide used in the process of the present invention can be any commercially available aluminum hydroxide with a mean particle size of below about 50 microns, preferably below 12 microns. Owing to the strong catalytic effect of the catalyst used there is no necessity to employ an expensive, finely divided aluminum hydroxide of the prior art with an average particle size of less than 2 microns in order to finish the reaction within a reasonable time.

In one embodiment, the herein described amounts of DMMP and aluminum hydroxide are mixed and the suspension formed is heated at the desired reaction temperature. In one embodiment, the catalyst can be added to the suspension of aluminum hydroxide in DMMP prior to, or after, the desired temperature has been reached. The catalyst can also be fed in during the heating of the suspension of aluminum hydroxide in DMMP. After the reaction has finished, the final slurry is evaporated to dryness, preferably under vacuum. According to a preferred embodiment of the invention, no filtrations or washings are used in the process. Optionally, if a washing, for example water washing or solvent washing, is desired, in order to remove any residual catalyst, it can be carried out, followed by filtration, thus optionally being a part of the process of the present invention.

Figure 7:
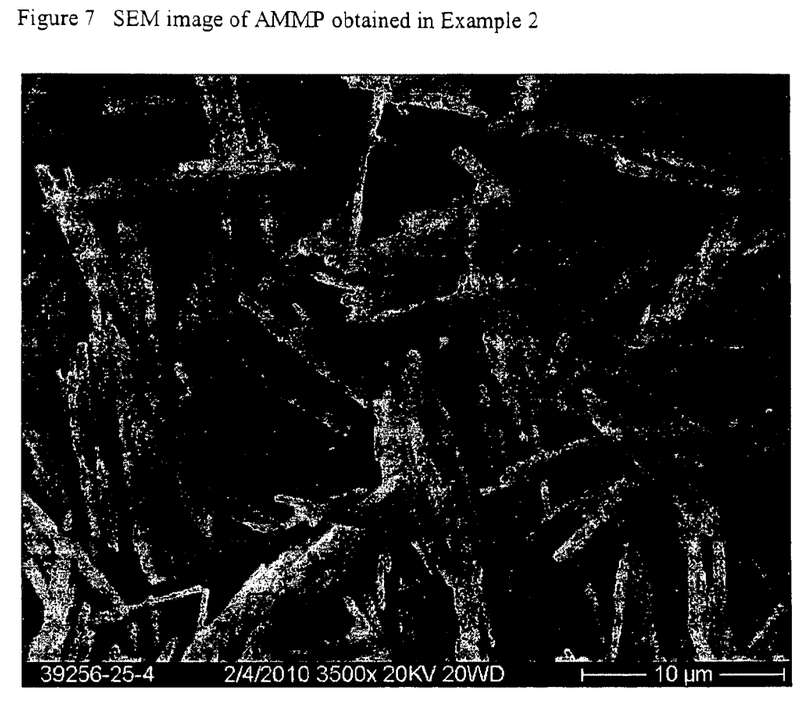
FIG. 7 is a scanning electron microscopy image of the AMMP obtained in Example 2.

The AMMP produced in the present invention has an average particle size of between about 1 to about 10 microns, preferably between about 2 to about 5 microns, and/or 90% of the particles of AMMP have a particle size of less than about 15 microns, preferably less than about 10 microns. The AMMP produced can be incorporated into a polymer in a granular form when there is a desire to avoid the handling of powdered AMMP. According to a preferred embodiment of the invention, granular AMMP can have a mean particle size of between about 200 to about 3000 microns, specifically 200 to about 2000 microns. In one embodiment herein, the AMMP produced herein can be seen as needle shaped crystals by scanning electron microscopy. In a specific embodiment herein, the needle shaped crystals of AMMP produced herein can be such as those indicated in the SEM images in FIG. 7 provided herein.

The process according to the invention provides AMMP in a good yield and with a high purity. The process of the invention herein produces AMMP in a yield of greater than about 90%, preferably greater than about 97%, based on ATH. AMMP is produced with a purity greater than 90%, preferably greater than 95%.

The AMMP of the invention is thermally very stable, as is evidenced by its TGA. The AMMP product has a TGA temperature for a 2% weight loss of in excess of 280° C. and, preferably, within the range of about 280 to about 315° C., and more preferably from about 290° C. to about 315° C. According to the TGA, the AMMP product loses 5% of its initial weight at a temperature in excess of about 300° C. and, preferably, within the range of from about 305° C. to about 325° C. The high TGA temperatures which are characteristic of the AMMP of this invention are believed to be due to the very high purity of the product. Such a complete or almost complete conversion of the aluminum hydroxide in the process of the invention results directly from the use of the phase transfer catalyst described herein.

In one further embodiment, there is provided herein a process comprising roller-compacting the AMMP produced in the manner described herein, into granular AMMP, preferably granular AMMP which is a free flowing material.

There is also provided herein a method of producing a flame retarded thermoplastic polymer comprising blending at least one thermoplastic polymer and aluminum methyl methylphosphonate as produced in the manner described herein. There is also provided a flame-retarded thermoplastic polymer containing AMMP produced by such a method. In one non-limiting embodiment, the thermoplastic polymer can already contain at least one flame retardant, e.g., hydroquinone bis-(diphenylphosphate) and melamine cyanurate prior to the addition of the AMMP produced in the manner described herein. In another embodiment, the flame-retarded thermoplastic polymer made by the process herein described can be a translucent or transparent polymer. The amount of AMMP used in such a method of blending with a thermoplastic polymer can be in an amount effective as a flame-retardant as determined by those skilled in the art, but can in one non-limiting embodiment, be from about 3 to about 30 weight percent, preferably from about 10 to about 30 weight percent, said weight percent being based on the weight of the polymer. In one non-limiting embodiment the thermoplastic polymer can be selected from the group consisting of thermoplastic polyesters, nylons, polycarbonate and its blends, polystyrene and its copolymers, polyethylene and its copolymers, polypropylene and its copolymers and combinations thereof. The AMMP of the invention herein can be used in any thermoplastic for which processing temperature doesn't exceed its decomposition temperature. For example, the AMMP of the invention can be used as a flame retardant additive in thermoset resins, in textiles and in coating applications, amongst others.

A number of illustrative and non-limitative embodiments of the invention will now be described, with reference to the examples below.

EXAMPLES

Analytical Methods

Thermogravimetric analysis (TGA) was used to test the thermal behavior of the product of the invention. The TGA values were obtained by the use of a TA Instruments Thermogravimetric Analyzer. Each sample was heated on a Pt pan from 25° C. to 450° C. at 10° C./min with a nitrogen flow of 50 ml/min.

Differential scanning calorimetry (DSC) was used to measure the melting temperature of crystalline products. The DSC measurements were obtained by using a TA Instruments DCS. A sample of 5-10 mg was sealed in an aluminum pan and heated from 25° C. to 450° C. at 10° C./min with a nitrogen flow of 50 ml/min Particle size distribution was measured using a Saturn DigiSizer 5200 V1.11. AMMP was dispersed in a mineral spirit (CAS 8052-41-3) using an ultrasonic disperser for 30 sec.

Scanning electron microscope (SEM) images showing the crystalline shape of the product were taken by a Scanning Electron Microscope Geol 5400.

The X-ray diffraction (XRD) "finger prints" were obtained by the use of an X-ray diffractometer Rigaku Ultima+. XRD was used to check the crystalline structure and the purity of the product of the invention.

Figure 1:
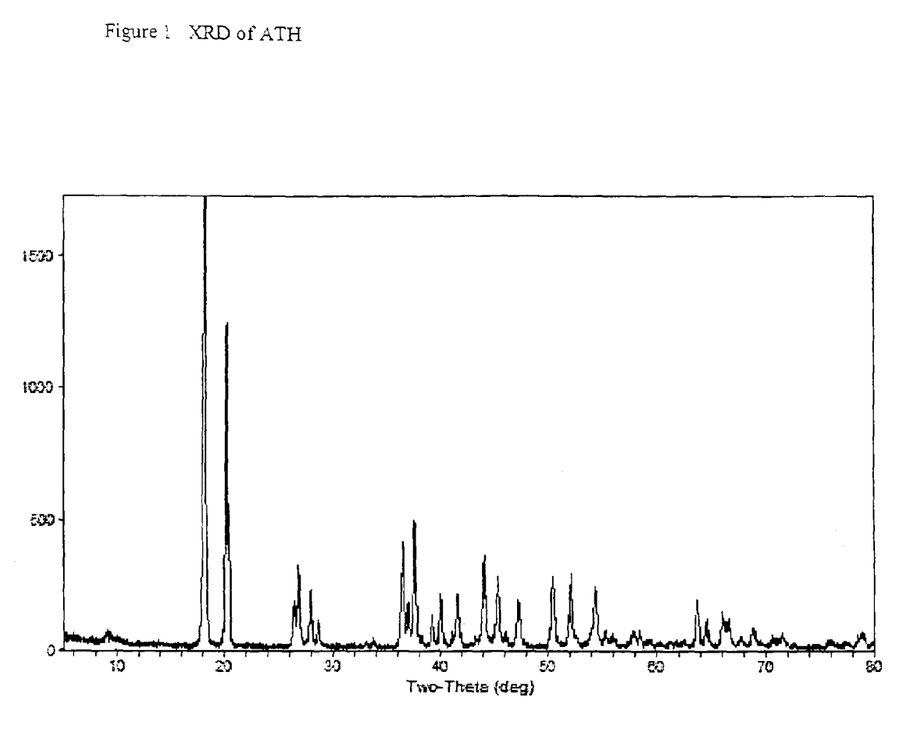
FIG. 1 is the X-ray diffraction fingerprint of aluminum hydroxide.

ATH produces its own XRD "finger prints" as shown in FIG. 1. Thus, the presence or absence of these ATH "finger prints" on the XRD of the product would indicate the degree of the ATH conversion.

TGA Of Aluminum Hydroxide

Figure 2:
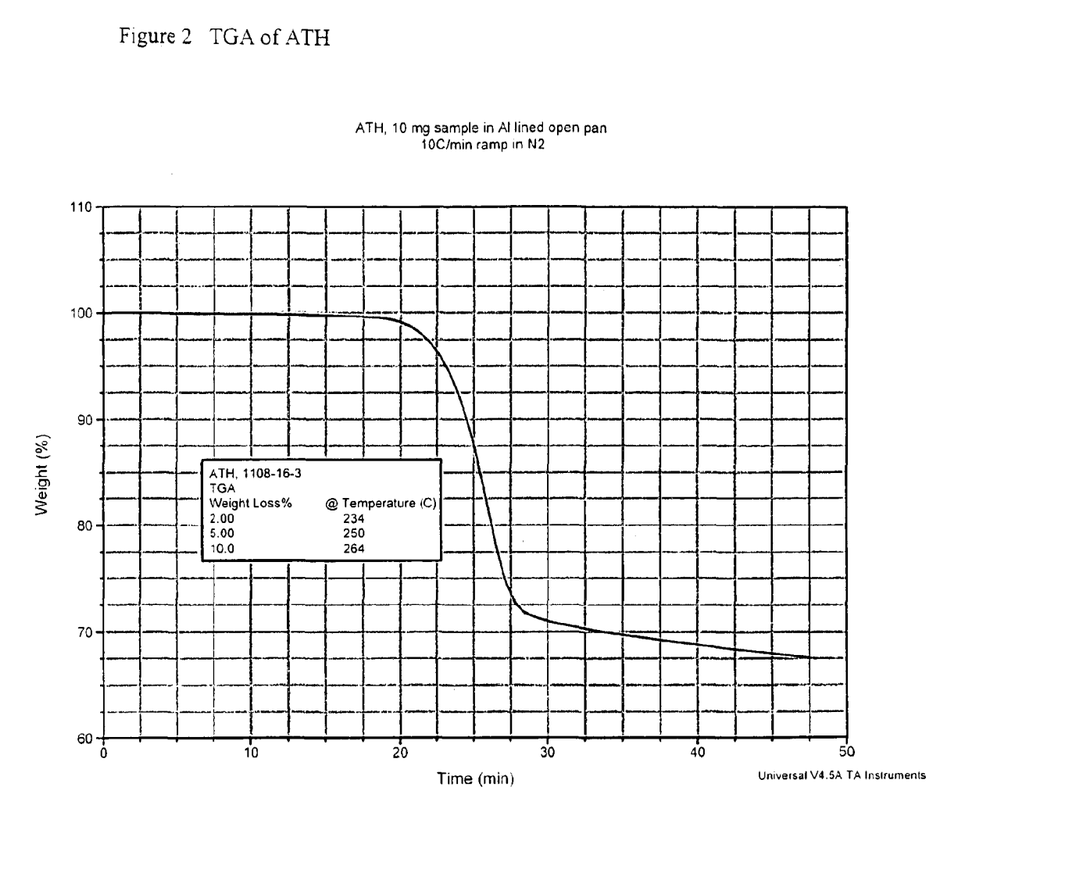
FIG. 2 is the thermogravimetric analysis of aluminum hydrodixe.

FIG. 2 shows the TGA of aluminum hydroxide (ATH). ATH starts to decompose at about 220° C. with a 2% wt. loss at 228° C. ATH ceased its main decomposition at about 280° C., with a weight loss of about 30%. Since ATH decomposes at a relatively lower temperature than AMMP, thermogravimetric analysis was selected to monitor the completion of the reaction of DMMP with ATH.

Setup Of Littleford Reactor

A Littleford Day, horizontal plow mixer, model DVT-22 or model DVT-130 with one 4" multi-blade chopper, was fitted with a vertical reflux condenser on its exhaust port. The condenser was supplied with atmospheric steam as its heating/cooling medium. In-line, but after the reflux condenser was a recovery condenser supplied with cold water to condense any vapors from the mixer vessel. The exhaust line from the mixer was set up so that it could easily be switched to a vacuum line that would allow for the quick removal of DMMP.

Comparative Example 1

Figure 3:
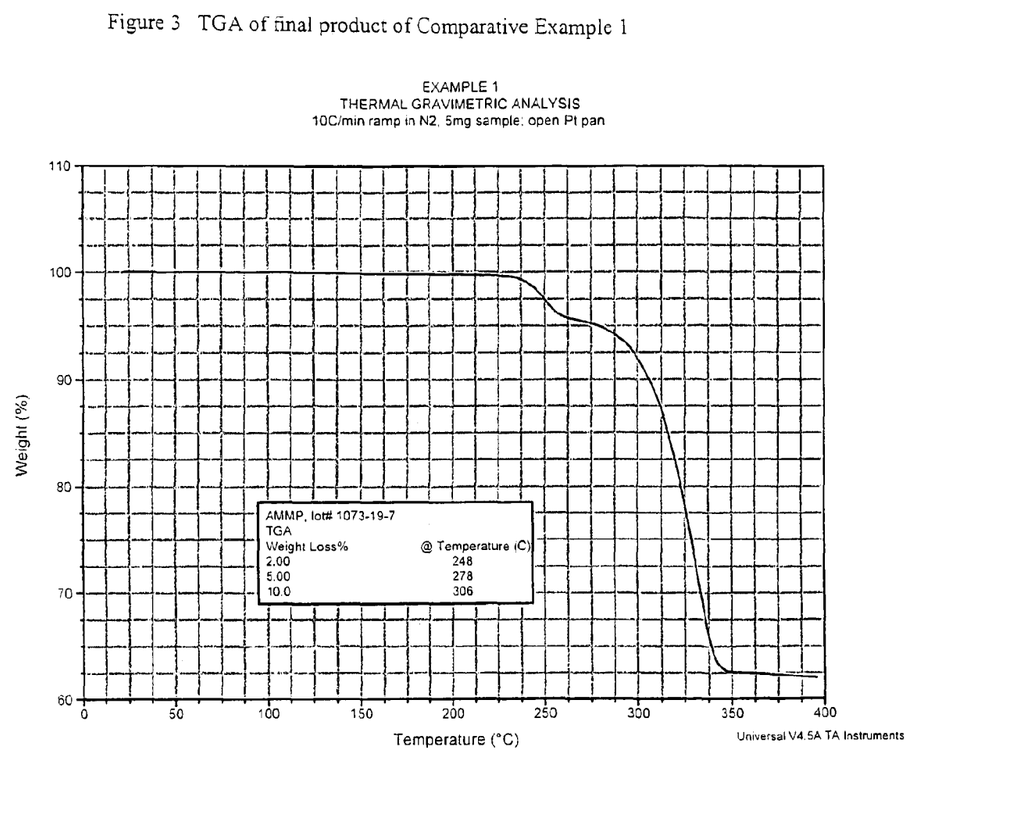
FIG. 3 is the thermogravimetric analysis of the final product of Comparative Example 1.

14.76 Kg (118.96 mol) of DMMP and 1.157 Kg (14.83 mol) of Al(OH)$_3$ were charged into the DVT-22 vessel and it was sealed. The horizontal plow mixer was set to a speed of 165 rpm. The chopper was set to a speed of 3600 rpm. A 1.5 standard liters per minute (slpm) N$_2$ purge was applied to the inside of the vessel and it was heated to reflux temperature. The first droplets of condensate appeared in the recovery condenser sight glass at a temperature of 177° C. The oil temperature in the reactor jacket was 210° C. for a period of 27 hours. At this time, vacuum was applied and the excess DMMP was removed. After cooling, 3.56 kg (63.90% yield) of a fine, white powder was removed from the vessel. FIG. 3 shows the TGA of the final product. The two-step decomposition pattern indicates that considerable amount of the ATH was not converted to AMMP. This unreacted ATH is responsible for low thermal stability of the final product.

Figure 4:
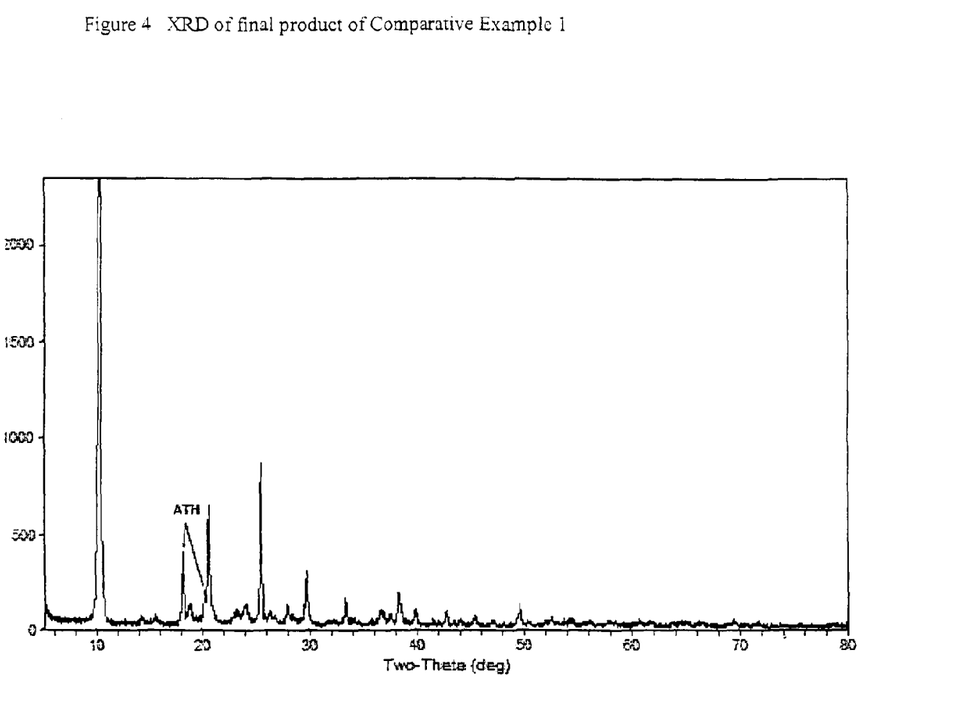
FIG. 4 is the X-ray diffraction of Comparative Example 1.

The presence of unreacted ATH can be seen on the product XRD shown in FIG. 4.

Example 2

Figure 5:
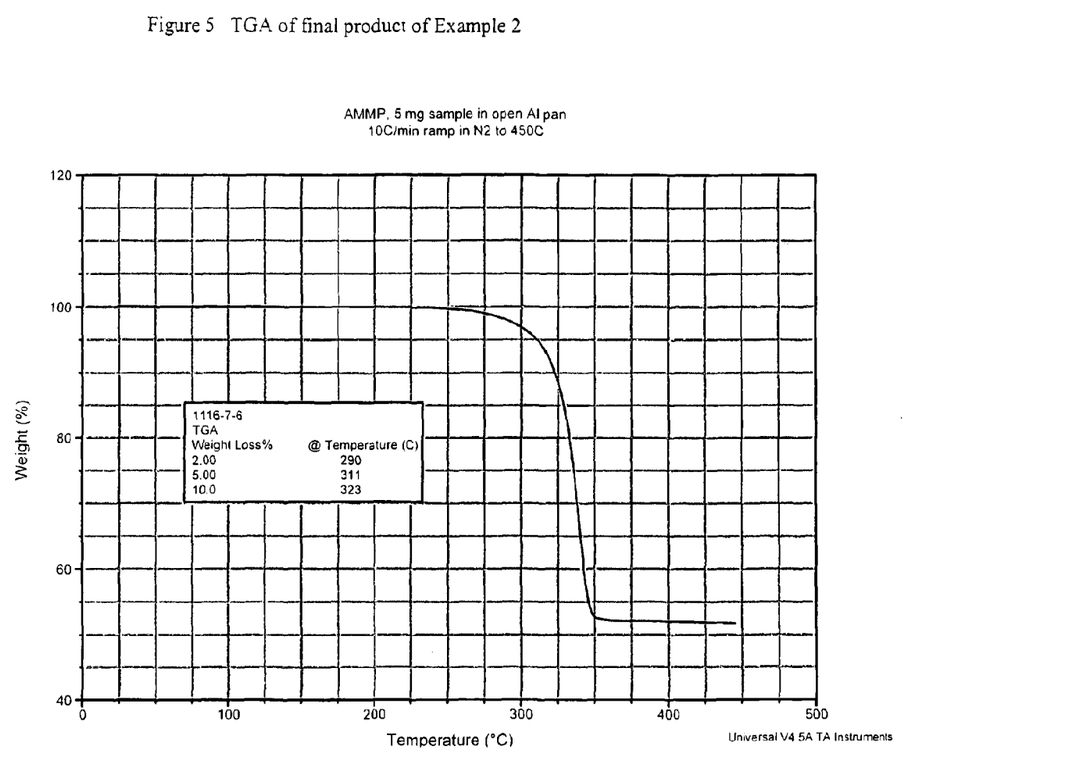
FIG. 5 is the thermogravimetric analysis of the final product of Example 2.

The same physical configuration, mixing speeds and N$_2$ purge were used as in Comparative Example 1. 94.6 kg (762.9 mol) of DMMP and 7.41 Kg (95 mol) of Al(OH)$_3$ were added to the DVT-130 vessel. In addition, 55.6 g of the phase transfer catalyst, tetra-n-butyl phosphonium bromide, was added. The vessel was sealed and heated to reflux temperature. The first drops of condensate appeared in the recovery condenser sight glass at a temperature of 174° C. The reaction was run for 9 hours maintaining it at the reflux temperature. The oil temperature in the reactor jacket was 210° C. At the end of the reaction, vacuum was applied and the DMMP was removed. A total of 32.1 kg (95.5% yield) of product was removed from the vessel. The thermogravimetric analysis of the final product is shown in FIG. 5. It had a very good thermal stability with a 2% weight loss at 290° C. This product had a one-step weight loss, which is indicative of a good conversion. The XRD spectrum of the AMMP product (FIG. 6) shows no traces of ATH. A scanning electron microscopy image of the AMMP obtained in this example is shown in FIG. 7. It is seen that AMMP prepared by this method has distinctive needle shaped crystals. Particle size distribution analysis was performed on this AMMP. The median particle size was measured at 2.8 microns and 90% of the particles had a particle size less than 7.9 microns.

A differential scanning calorimetry measurement was performed on this final product. No melting endotherm was detected before thermal decomposition. The only endotherm, with a minimum at 373° C., was attributed to thermal decomposition or volatilization.

Example 3

Figure 8:
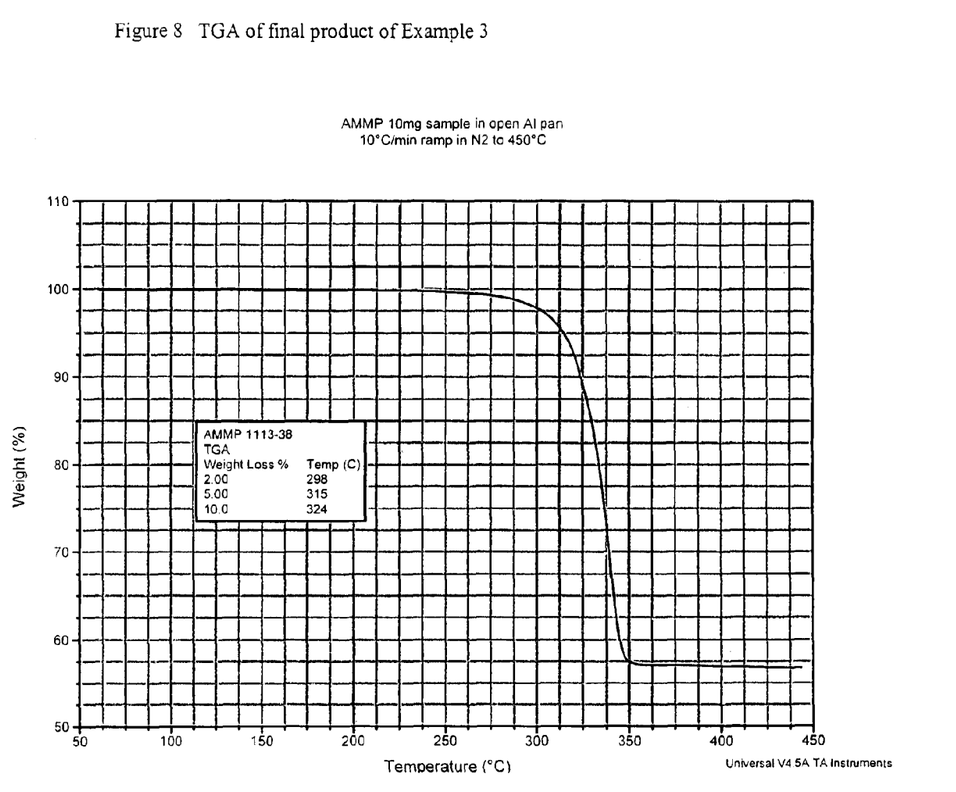
FIG. 8 is the thermogravimetric analysis of the final product of Example 3.

The same physical configuration, mixing speeds and N$_2$ purge were used as in Comparative Example 1. 94.6 kg (762.9 mol) of DMMP and 7.41 Kg (95 mol) of Al(OH)$_3$ were added to the DVT-130 vessel. In addition, 111.2 g of the phase transfer catalyst, tetra-n-butyl phosphonium bromide, was added. The vessel was sealed and heated to reflux temperature. The reaction was run for 7 hours maintaining it at the reflux temperature. The oil temperature in the reactor jacket was 210° C. At the end of the reaction, vacuum was applied and the DMMP was removed. A total of 32.4 kg (96.3% yield) of product was removed from the vessel. The final product was washed with water twice. The TGA of the final product is shown in FIG. 8. This product had a one-step weight loss, which is indicative of a good conversion. It had a very good thermal stability with a 2% weight loss at 298° C. A scanning electron microscopy image of the AMMP obtained in this example showed the same needle-shaped crystals as in Example 2.

Figure 6:
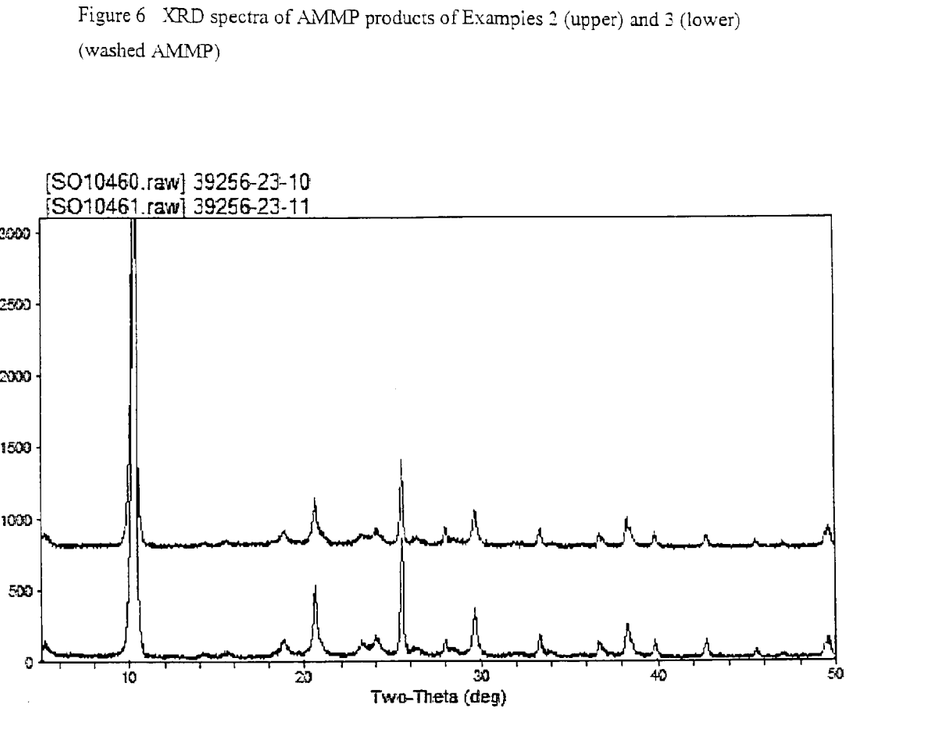
FIG. 6 is the X-ray diffraction spectra of the AMMP products of Examples 2 and 3.

FIG. 6 shows that the XRD spectrum of the AMMP of Example 3 is similar to that of Example 2. It is evident that washing does not affect the crystalline structure of the AMMP.

Example 4

Figure 9:
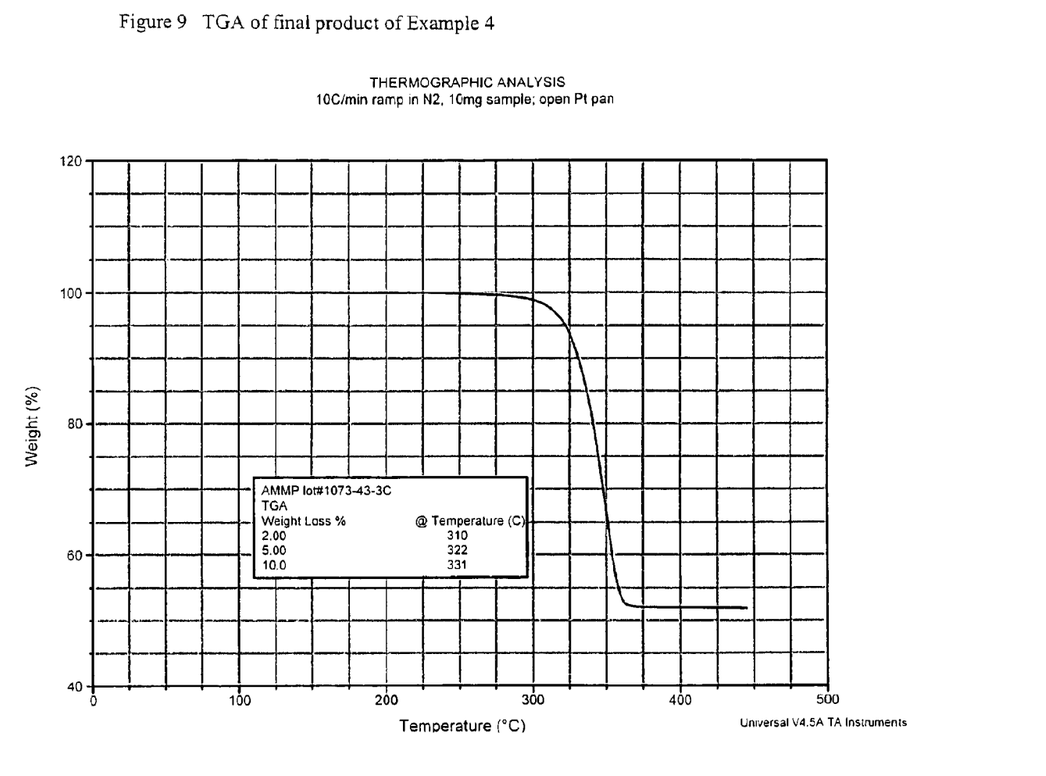
FIG. 9 is the thermogravimetric analysis of the final product of Example 4.

A 2-liter stainless steel, jacketed reactor was fitted with a vertical reflux condenser. The reflux condenser was supplied with hot water at 56° C. as a cooling/heating medium. A dry ice, cold finger was put in-line after the reflux condenser to condense any vapors from the reactor. 600 g (4.84 mol) of DMMP and 63 g (0.81 mol) of Al(OH)$_3$ were put in the reactor along with 1.26 g (0.004 mol) tetra-n-butyl phosphonium bromide (2% by weight based on Al(OH)$_3$). In addition, eight (8) 1 cm diameter ceramic mixing balls were added to the reactor and it was closed. The mixer was turned on and set at 500 rpm. A slight N$_2$ purge was applied to the reactor and hot oil was passed through the jacket. The first drop of condensate was observed after the reflux condenser at a reactor temperature of 165° C. The oil temperature was 210° C. The reactor was maintained at reflux for 12 hours, then cooled. The resulting product was a thick, gray suspension. A small portion of the suspension was put in an oven at 70° C. under vacuum overnight to remove the DMMP. The solid residue obtained was washed with methanol and then dried under vacuum overnight at 70° C. The thermogravimetric analysis of this final product is shown in FIG. 9. As seen, the thermal stability of AMMP is high, with 2% weight loss at 310° C.

Comparative Example 5

1.5 Kg (12.10 mol) DMMP was charged into a 3 liter reaction vessel and heated to 60° C. 484 g (12.10 mol) of sodium hydroxide was dissolved in 1000 g of deionized water in a separate vessel and charged into an addition funnel mounted on top of the reaction vessel. The sodium hydroxide solution was slowly added to the DMMP and the temperature was maintained between 75° C. and 90° C. The evolved methanol was collected in the condenser. The reaction was continued for another 1 hour at 70° C. after the addition of the sodium hydroxide was completed.

The reaction mixture was transferred to a 10 liter flask and diluted with 3.5 liters of deionized water. The pH of the solution was adjusted to 6.9-7 with HCl solution. 965 g (4.00 mol) of aluminum chloride hexahydrate was dissolved in 2.2 liters of deionized water in a separate 10 liter vessel. The reaction mixture prepared in step 1 (i.e., the addition of sodium hydroxide to DMMP and the steps thereafter described above) was slowly added to the aqueous aluminum chloride solution with continuous stirring. The obtained aqueous milky suspension was filtered. The obtained cake was washed with 500 ml of water and filtered again. The washing procedure was repeated 5 times.

Figure 10:
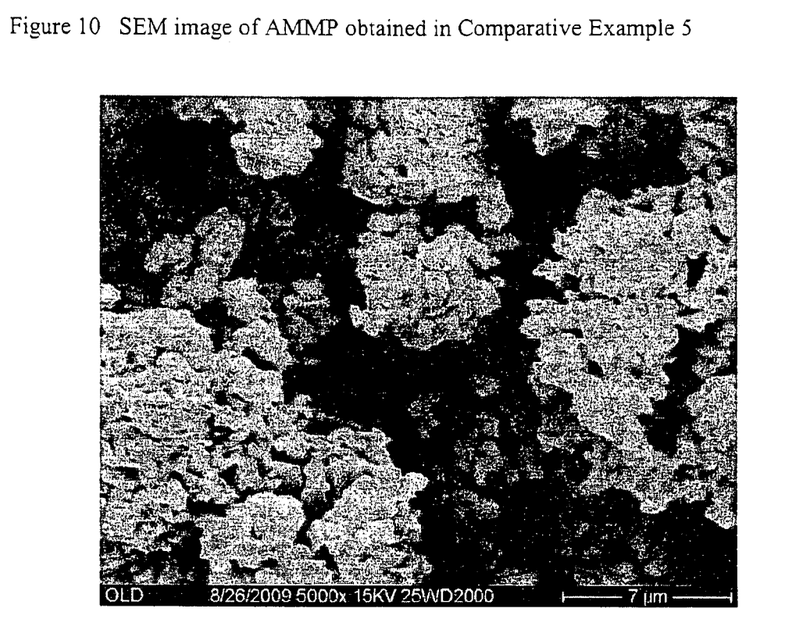
FIG. 10 is a scanning electron microscopy image of the AMMP obtained in Comparative Example 5.

The final material was dried at 70° C. in a vacuum oven. The dried material was mechanically ground and screened through a 100 mesh screen. FIG. 10 shows the SEM image of AMMP obtained in Comparative Example 5. As seen, this AMMP had a very different morphology to the AMMP prepared by the method of the invention (FIG. 7). Particle size distribution analysis was performed on this AMMP. The average particle size was measured at 11.3 microns and 90% of the particles had a particle size less than 29 microns.

Example 6

Dry Granulation Of Powdered AMMP Using Roller Compaction 800 g of the powdered product of Example 2 was compacted using a double-roll press (Hutt, Germany). The diameter of the roll was 22 cm, and its length was 6 cm. The roll compactor produced "curtain" shaped bodies. The force applied was 6 ton/cm and the rotation speed was 6 rpm. The material was recycled six times in the compactor in order to increase the strength of the compacts. The compacted material was then ground and sieved through 1 mm and 0.5 mm sieves. The fraction of granules with a size in the range of 0.5 to 1 mm was separated (400 g). The fines (below 0.5 mm, 400 g) were mixed with 400 g fresh powder, and the aforementioned compaction/grinding/sieving procedure was repeated several times to obtain a granular AMMP. The granular product had a bulk density of 0.55-0.6 g/cm³. The granules were composed of particulates having an average size of 2.3 micron, as determined by laser diffraction, and the particle size distribution was as follows: $d_{50}$ 0.3 micron, $d_{90}$ 5.6 micron.

The AMMP showed good compaction ability without using a binder. The final compacted AMMP exhibits the features of a free flowing material and therefore will be beneficial for consistent feeding to the extruders.

Example 7

In order to illustrate the invention, the following poly(butylene terephthalate) (PBT) thermoplastic composites were prepared (Table 1)

TABLE 1

| Composition of flame retardant thermoplastic | | |
|---|---|---|
| Material, producer | Function | Weight % |
| Poly(butylene terephthalate) PBT Celanex 2500 available from Ticona | Plastic matrix | 39.8 |
| Glass fibers for PBT, available for example, from Polyram | Reinforcing agents | 30.0 |
| Hydroquinone bis-(diphenylphosphate), HDP, available from ICL-IP America Inc. | Flame retardant | 10.0 |
| Aluminum Methyl Methylphosphonate (AMMP) available from ICL-IP America Inc. | Flame retardant | 10.0 |
| Melamine cyanurate FR-6120 granular available from ICL-IP America Inc. | Flame retardant | 10.0 |
| Hindered phenol Irganox 1010 available from Ciba | Heat stabilizer/ antioxidant | 0.2 |

Before compounding, the PBT pellets were dried in a circulating air oven ex Heraeus instruments at 120° C. for 4 hours. PBT and Irganox 1010 heat stabilizer were manually pre-mixed in a plastic bag. The mixture was fed, via the polymer feeder of a K-SFS 24 gravimetric feeding system ex. K-Tron to the main feeding port of the extruder. AMMP prepared in Example 2, HDP and FR-6120 were premixed in equal weight proportions 1:1:1 in the plastic bag. The thus obtained mixture of flame-retardants was fed via the powder feeder of the gravimetric feeding system ex. K-Tron to the main feeding port of the extruder. Glass fibers were fed via the lateral fiber feeder of the gravimetric feeding system to the 5$^{th}$ zone. Compounding was performed in a twin-screw co-rotating extruder ZE25 with L/D=32 ex Berstorff. The compounding temperature was set at 250-270° C. The screws rate was at 350 rpm and the feeding rate of the polymer (PBT) was at 15 kg/h. The extruded strands were pelletized in pelletizer 750/3 ex Accrapak Systems Ltd. The obtained pellets were dried in a circulating air oven ex Heraeus instruments at 120° C. for 4 hours. Standard test specimens were prepared by injection molding in the Allrounder 500-150 ex. Arburg. The injection molding was performed at 230-270° C. with a mold temperature of 90° C. Specimens were conditioned at 23° C. for 168 hours before testing. Results of the combustion tests and physical properties of the composites are presented in Table 2.

TABLE 2

| Flammability data and physical properties | | | | |
|---|---|---|---|---|
| | | | Source of AMMP | |
| | Test method | Example 2 | Example 3 | Example 6 |
| Physical property | | | | |
| Flammability vertical burning test at 1.6 mm | UL-94 | V-1 | V-1 | V-1 |

TABLE 2-continued

Flammability data and physical properties

| | Test method | Source of AMMP | | |
|---|---|---|---|---|
| | | Example 2 | Example 3 | Example 6 |
| Izod notched impact energy, J/m | ASTM D-256-81 Method C | 31.8 | 32.6 | 51.4 |
| Reversed notched test, J/m | ASTM D-256-81 Method E | 283 | 265 | 263 |
| HDT (Deflection temperature under flexural load of the test specimen), ° C. | Heat distortion test ASTM D648. Load 1820 kPa; heating speed 120° C./h. | 201 | 200 | 201 |
| Tensile properties | ASTM D638-95, v = 5 mm/min | | | |
| Strength, N/mm$^2$ | | 72.2 | 72.2 | 76.6 |
| Elongation at break, % | | 2.3 | 2.5 | 2.4 |
| Modulus, N/mm$^2$ | | 7640 | 7430 | 7600 |
| Melt flow index | ASTM D 1238 250° C./2.16 kg | 21 | 23 | 16 |
| Color gradient as molded vs. 100% white, DE | ASTM D-2244-79 | 6.8 | 6.8 | 6.5 |

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

The invention claimed is:

1. Aluminum methyl methylphosphonate in crystalline form wherein 90% of the aluminum methyl methylphosphonate particles have a particle size of less than 10 microns and where the aluminum methyl methylphosphonate has a thermogravimetric analysis temperature for a 2% weight loss of in excess of 280 degrees Celsius, and wherein the aluminum methyl methylphosphonate is obtained by the process of reacting aluminum hydroxide with dimethyl methylphosphonate in the presence of an efficient catalyst.

2. The aluminum methyl methylphosphonate of claim 1, wherein the catalyst is selected from the group consisting of a phase transfer catalyst, a thermally stable tertiary amine having a boiling point higher than about 140° C., a thermally stable phosphine having a boiling point higher than 140° C. and combinations thereof.

3. The aluminum methyl methylphosphonate of claim 2, wherein the phase transfer catalyst is a quaternary phosphonium salt selected from the group consisting of tetrabutylphosphonium chloride, tetrabutylphosphonium bromide, tetrabutylphosphonium iodide, tetrabutylphosphonium acetate complex, tetraphenylphosphonium chloride, tetraphenylphosphonium bromide, tetraphenylphosphonium iodide, ethyltriphenylphosphonium chloride, ethyltriphenylphosphonium bromide, ethyltriphenylphosphonium iodide, ethyltriphenylphosphonium acetate complex, ethyltriphenylphosphonium phosphate complex, n-propyltriphenylphosphonium chloride, n-propyltriphenylphosphonium bromide, propyltriphenylphosphonium iodide, butyltriphenylphosphonium chloride, butyltriphenylphosphonium bromide, butyltriphenylphosphonium iodide, ethyltri-p-tolylphosphonium acetate/acetic acid complex, ethyltriphenylphosphonium acetate/acetic acid complex, hexadecyltributylphosphonium bromide and combinations thereof.

4. The aluminum methyl methylphosphonate of claim 2, wherein the phase transfer catalyst is a quaternary ammonium salt selected from the group consisting of tetraethylammonium bromide, tetrabutylammonium chloride, tetrabutylammonium bromide, tetrabutylammonium hydrogen sulfate, methyl trioctylammonium chloride, benzyl triethylammonium chloride and combinations thereof.

5. The aluminum methyl methylphosphonate of claim 2, wherein the thermally stable tertiary amine having a boiling point higher than 140° C. is selected from the group consisting of 2-(dimethylamino)pyridine, 4-(dimethylamino)pyridine and combinations thereof.

6. The aluminum methyl methylphosphonate of claim 2 wherein the thermally stable tertiary amine having a boiling point higher than about 140° C. is selected from the group consisting of 1-methylimidazole; 2-methyl imidazole; 2-ethylimidazole; 2-propylimidazole; 2-butylimidazole; 2-pentylimidazole; 2-hexylimidazole; 2-cyclohexylimidazole; 2-phenylimidazole; 2-nonyl-imidazole; 2-undecylimidazole; 2-heptadecylimidazole; 2-phenyl-4-methylimidazole; 1-benzylimldazole; 1-ethyl-2-methylbenzimidazole; 2-methyl-5,6-benzimidazole; 1-vinylimidazole; 1-allyl-2-methylimidazole; 2-cyanoimidazole; 2-chloroimidazole; 2-bromoimidazole; 1-(2-hydroxypropyl)-2-methylimidazole; 2-phenyl-4,5-dimethylolimidazole; 2-phenyl-4-methyl-5-hydroxymethylimidazole; 2-chloromethylbenzimidazole; 2-hydroxybenzimidazole; 2-ethyl-4-methylimidazole; 2-cyclohexyl-4-methylimidazole; 4-butyl-5-ethylimidazole; 2-butoxy-4-allylimidazole; 2-carboethyoxy-butylimidazole; 4-methylimidazole; 2-octyl-4-hexylimidazole; 2-methyl-5-ethylimidazole; 2-ethyl-4-(2-ethylamino)imidazole; 2-methyl-4-mercaptoethylimidazole; 2,5-chloro-4-ethylimidazole; and mixtures thereof.

7. The aluminum methyl methylphosphonate of claim 2 wherein the thermally stable phosphine having a boiling point higher than 140° C. is selected from the group consisting of triaryl phosphines, alkyl diaryl phosphines, dialkyl aryl phosphines, trialkyl phosphines, where the aryl is a substituted or unsubstituted phenyl and the alkyl is a linear or branched or cyclic $C_4$-$C_{16}$ hydrocarbyl radical, and combinations thereof.

8. The aluminum methyl methylphosphonate of claim 7 wherein the thermally stable phosphine having a boiling point higher than 140° C. is triphenyl phosphine.

9. The aluminum methyl methylphosphonate of claim 1 having an average particle size of from about 2 to about 5 micron.

10. The aluminum methyl methylphosphonate of claim 1 which is in the form of needle shaped crystals as can be seen by scanning electron microscopy.

11. The aluminum methyl methylphosphonate of claim 1 wherein the molar ratio of dimethyl methylphosphonate to aluminum hydroxide is in the range of about 3 to about 15.

12. The aluminum methyl methylphosphonate of claim 1 wherein the molar ratio of dimethyl methylphosphonate to aluminum hydroxide is in the range of about 5 to about 10.

13. The aluminum methyl methylphosphonate of claim 1 wherein the concentration of said catalyst is in the range from about 0.1 to about 5 wt. % relative to said aluminum hydroxide.

14. The aluminum methyl methylphosphonate of claim 1 wherein the reaction temperature is between about 150 to about 181° C.

15. The aluminum methyl methylphosphonate of claim 1 wherein the TGA temperature for 2% weight loss is within the range of from about 280° C. to about 315° C.

16. The aluminum methyl methylphosphonate of claim 1 wherein the TGA temperature for 2% weight loss is within the range of from about 290° C. to about 315° C.

17. The aluminum methyl methylphosphonate of claim 1 wherein the TGA temperature for 5% weight loss is within the range of from about 300° C. to about 335° C.

18. The aluminum methyl methylphosphonate of claim 1 wherein the aluminum methyl methylphosphonate does not melt below 400° C.

19. A process comprising roller-compacting the aluminum methyl methylphosphonate of claim 1 into granular aluminum methyl methylphosphonate.

20. The process of claim 19 wherein the granular aluminum methyl methylphosphonate is a free flowing material.

21. A method of producing flame retarded thermoplastic polymer comprising blending thermoplastic polymer and the aluminum methyl methylphosphonate of claim 1.

22. A flame retarded thermoplastic polymer obtained according to the process of claim 21.

23. A process comprising reacting aluminum hydroxide with dimethyl methylphosphonate in the presence of an efficient catalyst to obtain the aluminum methyl methylphosphonate composition of claim 1.

24. The process of claim 23 wherein the catalyst is selected from the group consisting of a phase transfer catalyst, a thermally stable tertiary amine having a boiling point higher than 140° C., a thermally stable phosphine having a boiling point higher than about 140° C. and combinations thereof.

25. The process of claim 24 wherein the phase transfer catalyst is a quaternary phosphonium salt selected from the group consisting of tetrabutylphosphonium chloride, tetrabutylphosphonium bromide, tetrabutylphosphonium iodide, tetrabutylphosphonium acetate complex, tetraphenylphosphonium chloride, tetraphenylphosphonium bromide, tetraphenylphosphonium iodide, ethyltriphenylphosphonium chloride, ethyltriphenylphosphonium bromide, ethyltriphenylphosphonium iodide, ethyltriphenylphosphonium acetate complex, ethyltriphenylphosphonium phosphate complex, n-propyltriphenylphosphonium chloride, n-propyltriphenylphosphonium bromide, propyltriphenylphosphonium iodide, butyltriphenylphosphonium chloride, butyltriphenylphosphonium bromide, butyltriphenylphosphonium iodide, ethyltri-p-tolylphosphonium acetate/acetic acid complex, ethyltriphenylphosphonium acetate/acetic acid complex, hexadecyltributylphosphonium bromide and combinations thereof.

26. The process of claim 24 wherein the phase transfer catalyst is a quaternary ammonium salt selected from the group consisting of tetraethylammonium bromide, tetrabutylammonium chloride, tetrabutylammonium bromide, tetrabutylammonium hydrogen sulfate and methyl trioctylammonium chloride, benzyl triethylammonium chloride and combinations thereof.

27. The process of claim 24 wherein the thermally stable tertiary amine having a boiling point higher than 140° C. is selected from the group consisting of 2-(dimethylamino)pyridine, 4-(dimethylamino)pyridine and combinations thereof.

28. The process of claim 24 wherein the thermally stable tertiary amine having a boiling point higher than about 140° C. is selected from the group consisting of 1-methylimidazole; 2-methyl imidazole; 2-ethylimidazole; 2-propylimidazole; 2-butylimidazole; 2-pentylimidazole; 2-hexylimidazole; 2-cyclohexylimidazole; 2-phenylimidazole; 2-nonylimidazole; 2-undecylimidazole; 2-heptadecylimidazole; 2-phenyl-4-methylimidazole; 1-benzylimldazole; 1-ethyl-2-methylbenzimidazole; 2-methyl-5,6-benzimidazole; 1-vinylimidazole; 1-allyl-2-methylimidazole; 2-cyanoimidazole; 2-chloroimidazole; 2-bromoimidazole; 1-(2-hydroxypropyl)-2-methylimidazole; 2-phenyl-4,5-dimethylolimidazole; 2-phenyl-4-methyl-5-hydroxymethylimidazole; 2-chloromethylbenzimidazole; 2-hydroxybenzimidazole; 2-ethyl-4-methylimidazole; 2-cyclohexyl-4-methylimidazole; 4-butyl-5-ethylimidazole; 2-butoxy-4-allylimidazole; 2-carboethyoxy-butylimidazole; 4-methylimidazole; 2-octyl-4-hexylimidazole; 2-methyl-5-ethylimidazole; 2-ethyl-4-(2-ethylamino)imidazole; 2-methyl-4-mercaptoethylimidazole; 2,5-chloro-4-ethylimidazole; and mixtures thereof.

29. The process of claim 24 wherein the thermally stable phosphine having a boiling point higher than 140° C. is selected from the group consisting of triaryl phosphines, alkyl diaryl phosphines, dialkyl aryl phosphines, trialkyl phosphines, where the aryl is a substituted or unsubstituted phenyl and the alkyl is a linear or branched or cyclic $C_4$-$C_{16}$ hydrocarbyl radical, and combinations thereof.

30. The process of claim 24 wherein the thermally stable phosphine having a boiling point higher than 140° C. is triphenyl phosphine.

31. The process of claim 23 wherein the molar ratio of dimethyl methylphosphonate to aluminum hydroxide is in the range of about 3 to about 15.

32. The process of claim 23 wherein the molar ratio of the dimethyl methylphosphonate to the aluminum hydroxide is in the range of about 5 to about 10.

33. The process of claim 23 wherein the concentration of the catalyst is in the range from about 0.1 to about 5 wt. % relative to said aluminum hydroxide.

34. The process of claim 23 wherein the reaction temperature is between about 150 to about 181° C.

35. The aluminum methyl methylphosphonate of claim 2 wherein the phase transfer catalyst is selected from quaternary phosphonium salt and quarternary ammonium salt and combinations thereof.

* * * * *